United States Patent [19]

Lund

[11] 4,336,745
[45] Jun. 29, 1982

[54] SERVOVALVE FLOW LINEARIZATION CIRCUIT

[75] Inventor: Richard A. Lund, Chaska, Minn.

[73] Assignee: MTS Systems Corporation, Eden Prairie, Minn.

[21] Appl. No.: 123,720

[22] Filed: Feb. 22, 1980

Related U.S. Application Data

[63] Continuation of Ser. No. 929,573, Jul. 31, 1978, abandoned.

[51] Int. Cl.³ .................... F15B 21/02; F15B 13/16
[52] U.S. Cl. .............................. 91/35; 91/361; 91/433
[58] Field of Search ............... 91/433, 35, 361, 363 R, 91/363 A, 275

[56] References Cited

U.S. PATENT DOCUMENTS

| | | |
|---|---|---|
| 2,853,667 | 9/1958 | Booth et al. |
| 2,955,460 | 10/1960 | Stevens et al. |
| 3,260,273 | 7/1966 | Hayner |
| 3,442,120 | 5/1969 | Russenberger et al. |
| 3,488,999 | 1/1970 | Catonia |
| 3,508,159 | 4/1970 | Morpe |
| 3,664,358 | 5/1972 | Kosugi et al. |
| 3,699,989 | 10/1972 | O'Connor et al. |
| 3,718,033 | 2/1973 | Peterson |
| 3,727,520 | 4/1973 | McKown et al. ............ 91/433 |
| 3,741,073 | 6/1973 | Garnjost ...................... 91/433 |
| 3,751,994 | 8/1973 | Gross |
| 3,800,588 | 4/1974 | Larson et al. |
| 3,911,732 | 10/1975 | Larson |
| 3,918,298 | 11/1975 | Peterson et al. |
| 4,031,813 | 6/1977 | Walters et al. .............. 91/433 |
| 4,061,155 | 12/1977 | Sopha ......................... 91/433 |
| 4,078,749 | 3/1978 | Johnson, Jr. ................ 91/433 |

OTHER PUBLICATIONS

Sanders Associates, Inc.—Bulletin HD 3973 Rev. 1 Hydraulic Division.
Sanders Associates, Inc.—Bulletin HD 1973 Rev. 3 Hydraulic Division.
Sanders Associates, Inc.—Bulletin HD 10973 Rev. 3 Hydraulic Division.

*Primary Examiner*—Paul E. Maslousky
*Attorney, Agent, or Firm*—Kinney, Lange, Braddock, Westman and Fairbairn

[57] ABSTRACT

A linearization circuit for use with servovalves for controlling reciprocating actuators. The circuit will maintain a substantially linear flow as a function of spool position from the servovalve regardless of the differential pressure across the servovalve orifices, for example the differential pressures which result from changing direction of movement of the controlled actuator under a high load. A differential pressure signal from the actuator, which correlates to differential pressure on the servovalve orifices is processed to provide a compensation signal combined with the normal control signal to achieve the desired output.

5 Claims, 2 Drawing Figures

SERVOVALVE FLOW LINEARIZATION CIRCUIT

This is a continuation of application Ser. No. 929,573, filed July 31, 1978 now abandoned.

BACKGROUND OF THE INVENTION

1. Field of the Invention

The present invention relates to controls for servovalves which are used for operating actuators under cyclic load conditions.

2. Prior Art

In the prior art various compensation circuits for controlling servovalves through feedback loops have been advanced. Many of these also sense a differential pressure on an actuator for providing feedback signals for different methods of control. For example U.S. Pat. Nos. 3,800,588; 3,911,732; and 3,918,298 show multiple actuator control systems which employ various types of feedback from transducers for controlling servovalves in response to load conditions at other than the controlled actuator.

Likewise, U.S. Pat. No. 3,718,033 illustrates a testing apparatus utilizing servovalve controlled actuators with a cross coupling arrangement between actuators operating along axes which are at right angles with respect to each other. This patent also discloses the use of a shaping network for providing an output signal on a nonlinear basis to its input signal for compensation.

A typical feedback loop is shown in U.S. Pat. No. 2,955,460. In relation to mechanical systems, a method of providing compensating pressures acting directly on a spool valve to attempt to maintain uniform differential pressure on the spool is disclosed in U.S. Pat. No. 3,260,273. The same type of devices are sold by Sanders Associates, Inc. Hydraulic Division, Manchester, New Hampshire, for example their Model FT10A4 and similar units which involve a type of mechanical flow control. These valves generally have quite slow responses, and are not suitable for high frequency operation in which environment most servovalves must operate for adequate testing at the present time.

Additional patents showing devices of interest include U.S. Pat. Nos. 3,488,999; 3,699,989; 3,664,358; and 2,853,667. These patents represent the state of the art uncovered in a preliminary search.

SUMMARY OF THE INVENTION

The present invention relates to a control circuit for servovalves which provides for a linear output flow even at relatively high frequency sinusoidal loading of the actuators. In testing operations, for example in fatigue testing with high mean loads and a cyclic superimposed load, or in "shaker" testing the actuator will be under load in one direction of movement of the actuator, and then when moving in opposite direction it must hold the load back. The differential pressure on the servovalve will vary depending on the direction of movement of the actuator, causing a variation in fluid flow which can be highly nonlinear with direction of movement of the actuator. Many attempts have been made to correct for this, but at relatively high frequencies of operation, for example in the range of 30 to 40 Hz achieving the desired load peaks during each cycle of operation is difficult with existing circuitry.

In most servovalves, the valve control is in response to what is termed an error signal control. A command is utilized to control the servovalve in a closed loop arrangement whereby the input signal is compared with a feedback signal. The feedback generally is a stroke feedback loop in the normal manner shown in several prior art patents cited above.

In the present device the differential pressure on the actuator is sensed, and is correlated to the position of the spool. The need for correlation to spool position is due to the changing differential pressure on the spool at each change of actuator stroke direction. As shown, a signal comprising the differential pressure on the controlled actuator divided by the supply pressure is provided to a shaping network or circuit that is designed to provide an output which is a known function of the input signal and spool position. This function generator or shaping circuit is designed to provide a desired compensation signal which is combined with the control error signal in a multiplier, and this multiplied signal is then summed with the error signal and is used as the drive signal to the servovalve. The servovalve spool is compensated to provide a uniform flow throughout its range of operation and thus provide a more exact load or stroke control.

DESCRIPTION OF THE PREFERRED EMBODIMENT

Figure 1:
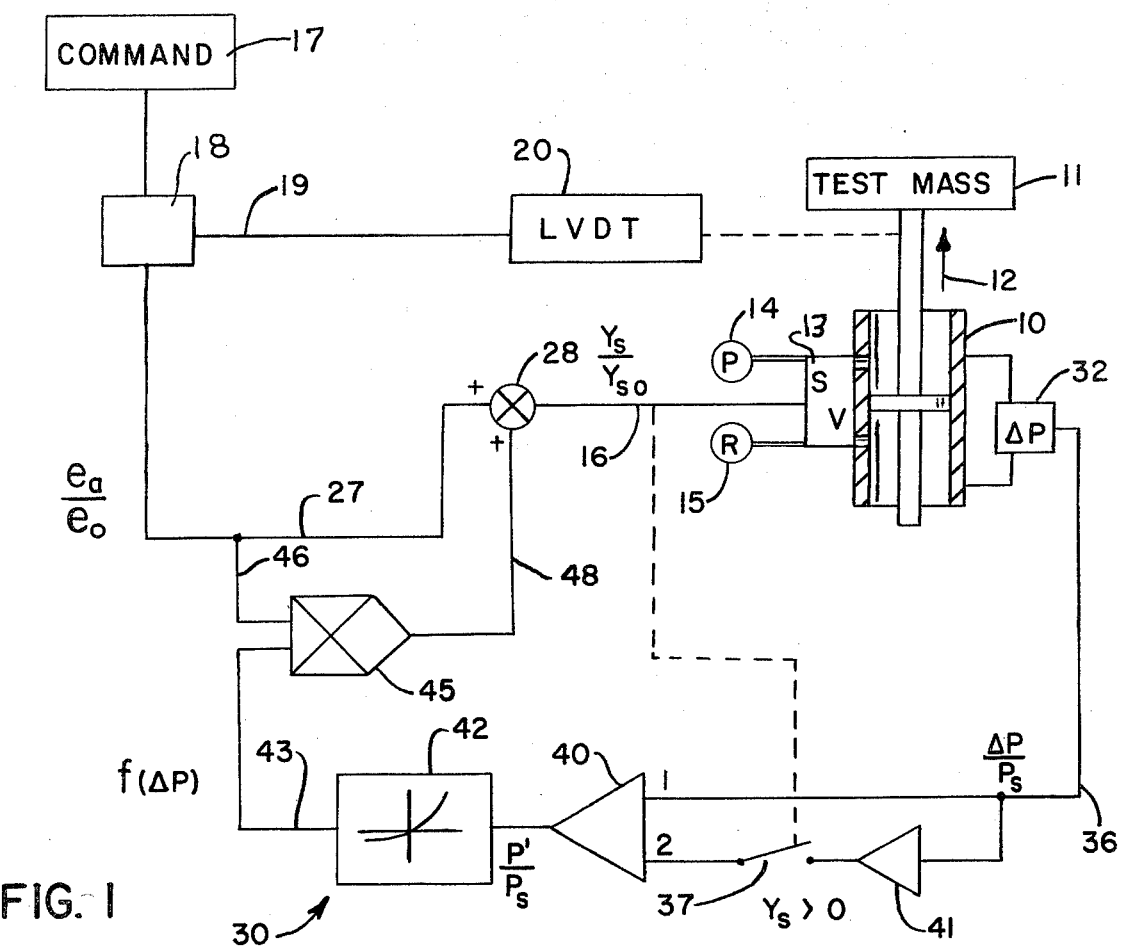
FIG. 1 is a schematic representation of a circuit diagram utilized to carry out the present invention.

Referring to FIG. 1, a schematic representation of a shaker test setup utilizing the compensation circuit made according to the present invention is illustrated for explanatory purposes.

The test device as shown includes hydraulic motor means, as shown, a double acting hydraulic actuator indicated generally at 10 which in turn shakes or moves a test mass or load indicated at 11 in a reciprocating or cyclical path.

The reciprocating actuator 10, during its operation in an upward direction as indicated by arrow 12, requires a high pressure on one side of the internal piston, and in an opposite direction of movement the rate of movement of the test mass is controlled so that the actuator holds back the test mass.

During this reciprocal or cyclic load operation, the actuator movement is controlled through a servovalve control indicated generally at 13. The servovalve has suitable pressure and return connections 14 and 15 as shown, and has an internal servovalve spool which is driven by a signal $y_s/y_{s0}$ (which represents spool position divided by spool full open position) applied along a line 16 to the servovalve drive. The servovalve has passageways open to provide pressure and return fluid paths to opposite sides of the piston in the actuator 10 as shown.

The normal servovalve circuitry includes a command program function generator 17, which delivers an output signal representing the desired program for the controlled actuator to a summing circuit 18 that combines the command signal with a feedback signal provided on a line 19 from a transducer 20. The feedback signal may be stroke feedback. If a stroke feedback is used the transducer 20 will be an LVDT transducer and the signal represents the actual position of the actuator. Force feedback may be used for control and would be dependent on a load cell or pressure transducer signal. The feedback permits comparison to determine that the program provided by generator 17 is being followed by the actuator. This cycling or reciprocation of the actuator is controlled by the program from function generator 17. The circuit 18 delivers an error signal output along a line 27 which represents the change at the actuator needed to follow the program command signal.

In this particular instance, a normalized or percentage of full scale signal is used for controlling the servovalve. The voltage output on line 27 is representative of the quantity ($e_a$) /($e_{a0}$) . The $e_{a0}$ term represents the maximum expected error, and $e_a$ is the error signal developed for controlling the servovalve and thus the actuator.

Line 27 is connected to a summing junction 28, and this signal is summed with the compensation signal and provided to line 16 for controlling the servovalve in accordance with the desired program. The output on line 16 is representative of the spool position ($y_s$) divided by the spool position at full flow ($y_{s0}$).

In order to obtain linear flow across the servovalve 13 during movement of the actuator 10 in both directions as the actuator follows the command signal, a compensating circuitry indicated generally at 30 is provided. This compensating circuitry utilizes a differential pressure signal providd along a line 36 from a differential pressure transducer 32 that is connected to sense pressure on the opposite sides of the actuator piston. The sensor for differential pressure may also sense pressure directly at the servovalve. The signal on line 36 correlates with the differential pressure on the servovalve. The voltage output along a line 36 is scaled to represent differential pressure across the actuator ($\Delta P$) /($P_s$) ·$P_s$ represents the supply pressure.

The output along line 36 is provided to a "one" input of a summing amplifier 40. The summing amplifier 40 has a "two" or doubling input, and this doubling input is connected through an electronic switch 37 to the output of a sign inverting amplifier 41, which has its input also connected to line 36. A plus quantity into amplifier 41 provides a minus quantity out.

The switch 37 is opened and closed in response to the sign of the spool command signal to servovalve 13. If desired a sensor may be provided to determine spool position to control switch 37.

When the switch 37 is open, the summing amplifier 40 provides an output that is the same as its one input, namely $\Delta P/P_s$, which is represented as $P'/P_s$ at the output. However, when the switch 37 is closed, the output of the summing amplifier 40 will be a negative value and therefore equal to a negative $(-)\Delta P/P_s$. The output of inverter 41 is negative and this is doubled in amplifier 40 and summed with the positive input from line 36.

Figure 2:
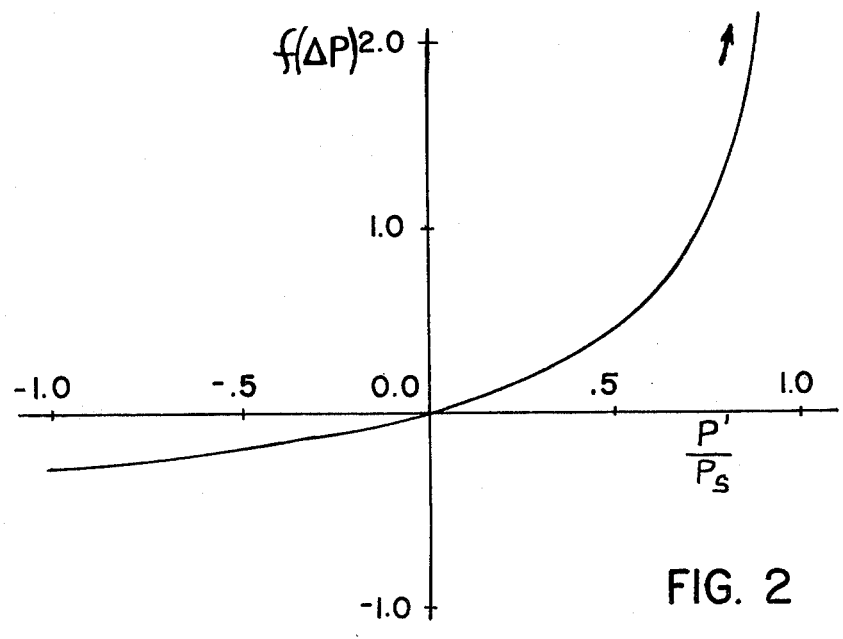
FIG. 2 is a graphic representation of a typical function used for providing compensation in the circuit of FIG. 1.

The output of amplifier 40 is provided to a shaping network circuitry represented at 42. The shaping network circuitry 42 can be a diode shaping network or a desired function generator that provides a compensation signal output along a line 43, which signal is nonlinear in relation to the input signal as shown schematically in the graph represented within the circuit 42. The shaping network adjusts for the gain of the signal at its input. The particular function that is typical for the applications involved here is shown in FIG. 2 in greater detail. The functions may be calculated from equations (10) set out in later portions of this specification.

The output along line 43 thus is a function of the differential pressure on the servovalve spool. This function is provided to one input of a multiplier 45, which has its other input connected by a line 46 to line 27. The output of the multiplier along line 48 then is connected to the summing junction 28, and the drive signal along line 16 is a normalized compensated signal which represents the spool position command signal divided by a signal representing the spool in its full open position.

The switch 37 is closed when the spool position signal on line 16 is positive, and is switched open when the spool position signal on line 16 is negative. Therefore the switch 37 is merely a spool position sensitive switch which provides the correct compensation when the spool moves from positive drive to negative position or vice versa.

As previously stated, the nonlinear flow is pronounced in high mean load fatigue tests with a cyclic load superimposed on the mean load. The cyclic load varies with time as the actuator is reciprocated. The nonlinear flow also occurs in shaker testing which is schematically shown in the drawings for explanatory purposes.

The servovalve must hold the load back as well as drop the entire supply pressure when the actuator is moving in one direction, as opposed to regulating the supply pressure into the actuator to apply the load when the actuator is moving in the opposite direction. Clearly, in the first direction the total pressure drop across the servovalve may be considerably greater than supply pressure, while in the other direction the pressure drop may be considerably less than supply pressure. Thus, the flow (or velocity) gain can be highly nonlinear with direction. The circuit described is analyzed for the case of negligible servovalve spool dynamics.

Flow across a servovalve may be described in scaled form by $$\frac{q}{q_0} = K \sqrt{\frac{\Delta P_{s/v}}{P_s}} \frac{y_s}{y_{s0}} \quad (1)$$

where q is flow, $q_0$ is flow at a spool full open position (a number less than or equal to 1) $y_s$ is spool position, $y_{s0}$ represents the spool full open position, $\Delta P_{s/v}$ is the pressure drop across the servovalve, and $P_s$ is supply pressure. For a linear flow gain it is required to have $$\frac{q}{q_0} = K \frac{y_s}{y_{s0}} \quad (2)$$

so that the servovalve command must be effectively divided by $\sqrt{\Delta P_{s/v}/P_s}$. If $e_a/e_{a0}$ is the scaled command ($e_a$ is error signal and $e_{a0}$ is maximum error signal) to the servovalve, then the spool position becomes:

$$\frac{y_s}{y_{s0}} = \frac{1}{\sqrt{\Delta P_{s/v}/P_s}} \frac{e_a}{e_{a0}} \quad (3)$$

It is desirable to avoid a divide operation on the input signal because of potential instability. It also is desirable to implement a correction in parallel with the normal valve drive signal. This may be done by first writing equation (3) as $$\frac{y_s}{y_{s0}} = \left[\frac{\Delta P_{s/v}}{P_s}\right]^{-\frac{1}{2}} \frac{e_a}{e_{a0}} \quad (4)$$

and then further modifying equation (4) to obtain $$\frac{y_s}{y_{s0}} = \left\{1 + \left[\left(\frac{\Delta P_{s/v}}{P_s}\right)^{-\frac{1}{2}} - 1\right]\right\} \frac{e_a}{e_{a0}} \quad (5)$$

The servovalve pressure drop may be sufficiently accurately established from the actuator differential pressure signal ($\Delta P$). If $\Delta P$ is defined as the pressure drop across the actuator in the positive direction, and $P_s$ represents supply pressure, then $$\frac{\Delta P_{s/v}}{P_s} = \begin{cases} 1 - \Delta P/P_s, y_s > 0 \\ 1 + \Delta P/P_s, y_s < 0 \end{cases} \quad (6)$$

if fixed orifice pressure drops are neglected.

Next, it is convenient to define $$\frac{P'}{P_s} = \begin{cases} \Delta P/P_s, y_s > 0 \\ -\Delta P/P_s, y_s < 0 \end{cases} \quad (7)$$

from which equation (6) can be written $$\frac{\Delta P_{s/v}}{P_s} = 1 - \frac{P'}{P_s} \quad (8)$$

Now, equation (5) can be written $$\frac{y_s}{y_{s0}} = [1 + f(\Delta P)] \frac{e_a}{e_{a0}} \quad (9)$$

with f ($\Delta P$) defined as $$f(\Delta P) = \left(\frac{P'}{P_s}\right)^{-\frac{1}{2}} - 1 \quad (10)$$

This function is plotted in FIG. 2 and represents the output of circuit 42.

The overall circuit may be simplified in some cases by approximating f ($\Delta P$) rather than providing a function generator to provide the nonlinear output. A straight line approximation should give good results for servovalve pressure drops up to and probably exceeding $P_s/2$. In all cases, f ($\Delta P$) is limited in value for positive actuator pressure drops approaching supply pressure.

The effect of spool dynamics may be compensated for effectively providing series compensation to the valve drive signal. This is done during the normal "tuning" of a servovalve.

The circuit shown thus provides compensation to obtain a linear flow gain across the servovalve during operation, and obtaining more precise load control of an actuator at high velocities and high loads.

The compensation circuit may also be used to adjust position of a three way servovalve controlling a single acting actuator as well. Further, various hydraulic motor devices, rotary or linear, may be controlled by the servovalve.

What is claimed is:

1. A flow control linearizing circuit for obtaining desired flow rates from a servovalve having a spool and having a pair of output passageways coupled to an actuator having means for reciprocating a load in a loading cycle which results in different differential pressures at the output passageways of the servovalve during the loading cycle, the flow in said output passageways being a function of a spool position input command signal provided to said servovalve and which changes in sign between negative and positive during the loading cycle, and including means providing an error control signal representing a combined programmed command signal and feedback signal, wherein the improvement comprises means to compensate the error control signal including means to provide a signal representative of the differential pressure at the output passageways of the servovalve during operation, means to process said signal from said means to provide and to deliver a processed signal which is a desired function of the signal from the means to provide and is correlated to the sign of the spool position input command signal, function generator means coupled to said means to process to provide a predetermined output compensation signal as a function of said processed signal, and means to combine said compensation signal with said error control signal to adjust the error control signal as a function of the signal representing differential pressure and provide an output comprising the spool position input command signal whereby the spool position input command signal controls the servovalve to provide output flows from the servovalve that are substantially linear during changes of said differential pressure at the output passageways.

2. The combination as specified in claim 1 wherein said means to provide comprises differential pressure sensing means having an output representative of the differential pressure at the output passageways of said servovalve during a full loading cycle.

3. In combination with a closed loop servo control apparatus including an actuator having a reciprocating portion, a servovalve having a spool and controlling flow of fluid under pressure to reciprocate the actuator, and a control loop including means providing a program command signal, means providing a feedback signal from the actuator, and means to combine the program command signal and the feedback signal to provide an error signal representing the error between the programmed command signal and the feedback signal; the improvement comprising a compensating circuit to modify the error signal and provide a control signal controlling spool position to the servovalve compensated to provide flow from the servovalve which is equal to the desired flow regardless of the differential pressure at the output of said servovalve during cyclic loading wherein the sign of the control signal changes between positive and negative, comprising first means to provide a first signal representative of the differential pressure on the servovalve output, processing means to process said first signal including means responsive to the sign of the control signal to modify said first signal when the control signal sign is negative, function generator means having an input and a compensation signal output, said compensation signal output being at a known relationship to the signal at said function generator input, said function generator input being connected to said processing means, and means to combine the compensation output of said function generator and said error signal to form said control signal.

4. In combination, a hydraulic motor means having an internal element responsive to differential pressures for driving a load in a reciprocating path under such differential pressures, a servovalve having a pair of output passageways controlling flow of hydraulic fluid under pressure to said motor means, feedback means on the motor means to provide a signal indicating the actual state of a monitored condition of the motor means, means to provide a command signal to establish a program control for said servovalve, means to combine said command signal and said feedback signal from the motor means to provide an error control signal for said servovalve, and a compensation circuit to provide a compensation signal to compensate the error control signal for changes in differential pressure on the servovalve output passageways and establish substantial linear flow of hydraulic fluid under pressure to the motor means as the motor means internal element moves in its reciprocating path, means connected to receive and combine the compensation signal and the error control signal and connected to the servovalve to provide a final control signal for said servovalve, said final control signal being such that it changes between positive and negative as the motor means moves the load in its reciprocating path, said compensation circuit further comprising function generator means having an input and an output, first means to provide to said function generator input a first signal which is a function of differential pressure on the servovalve output passageways when the control signal is positive, second means to provide to the function generator input a second signal comprising the first signal multiplied by a minus one when the final control signal is negative, the function generator means providing said compensation signal at its output, the compensation signal being represented as $f(\Delta P)$ and being generally of the form $$f(\Delta P) = 1 - \left(1 - \frac{P'}{P_s}\right)^{\frac{1}{2}} - 1,$$

wherein $\Delta P$ represents a function of differential pressure at said servovalve output passageways, $P'$ represents the respective first and second signals, and $P_s$ represents the pressure of the supply of hydraulic fluid under pressure, and means to couple the output of the function generator means to the means connected to receive and combine.

5. The combination of claim 4 wherein the final control signal is represented by the quantity $y_s/y_{s0}$ and wherein the final control signal represents the quantity $$\frac{y_s}{y_{s0}} = [1 + f(\Delta P)] \frac{e_a}{e_{a0}}$$

where $e_a/e_{a0}$ is the error control signal and represents the actual error signal as provided by the means to combine the command signal and the feedback signal divided by the maximum expected error signal.

* * * * *